(12) United States Patent
Gabbay

(10) Patent No.: US 6,355,065 B1
(45) Date of Patent: Mar. 12, 2002

(54) IMPLANTABLE SUPPORT APPARATUS AND METHOD OF USING SAME

(76) Inventor: Shlomo Gabbay, #1 Randall Dr., Short Hills, NJ (US) 07078

( * ) Notice: Subject to any disclaimer, the term of this patent is extended or adjusted under 35 U.S.C. 154(b) by 0 days.

(21) Appl. No.: 09/388,416

(22) Filed: Sep. 1, 1999

(51) Int. Cl.⁷ .................................................. A61F 2/00

(52) U.S. Cl. ..................... 623/11.11; 606/151

(58) Field of Search ........................... 623/11.11, 14.13, 623/14.12, 15.11, 23.64, 23.72; 606/151, 150, 148; 600/37

(56) References Cited

U.S. PATENT DOCUMENTS

| | | | | |
|---|---|---|---|---|
| 2,587,966 A | * | 3/1952 | Cleary | 606/151 |
| 5,290,217 A | * | 3/1994 | Campos | 606/151 |
| 5,441,508 A | * | 8/1995 | Gazielly et al. | 606/151 |
| 5,468,242 A | * | 11/1995 | Reisberg | 606/151 |

OTHER PUBLICATIONS

Product Brochure for Shelhigh No–React Pericardial Patch, (2 pgs).

"Long–Term Outcome and Quality of Life After Modified Pubovaginal Sling for Intrinsic Sphincteric Deficiency", by Mohamed F. Hassouna and Gamal M. Ghoniem, Urology, vol. 53, pp. 287–291, 1999.

"Use of the Fascial Sling for Neurogenic Incontinence: Lessons Learned", by Ross M. Decter, pp. 683–686, The Journal of Urology, vol. 150, pp. 683–686, Aug. 1993.

Instructions for Use, "In–Fast Bone Screw System for Transvaginal Cystourethropexy and Vaginal Sling Procedures", Influence Medical Technologies Ltd., 1997 (8pgs).

* cited by examiner

Primary Examiner—David J. Isabella
(74) Attorney, Agent, or Firm—Amin & Turocy, LLP

(57) ABSTRACT

An implantable support apparatus includes a sheet of a flexible biocompatible material having apertures formed through end portions thereof to provide suture holes. A plurality of relatively larger apertures are formed through an intermediate portion of the sheet located between the end portions of the sheet to promote adhesion and improve integration of the apparatus into a patient's body.

12 Claims, 1 Drawing Sheet

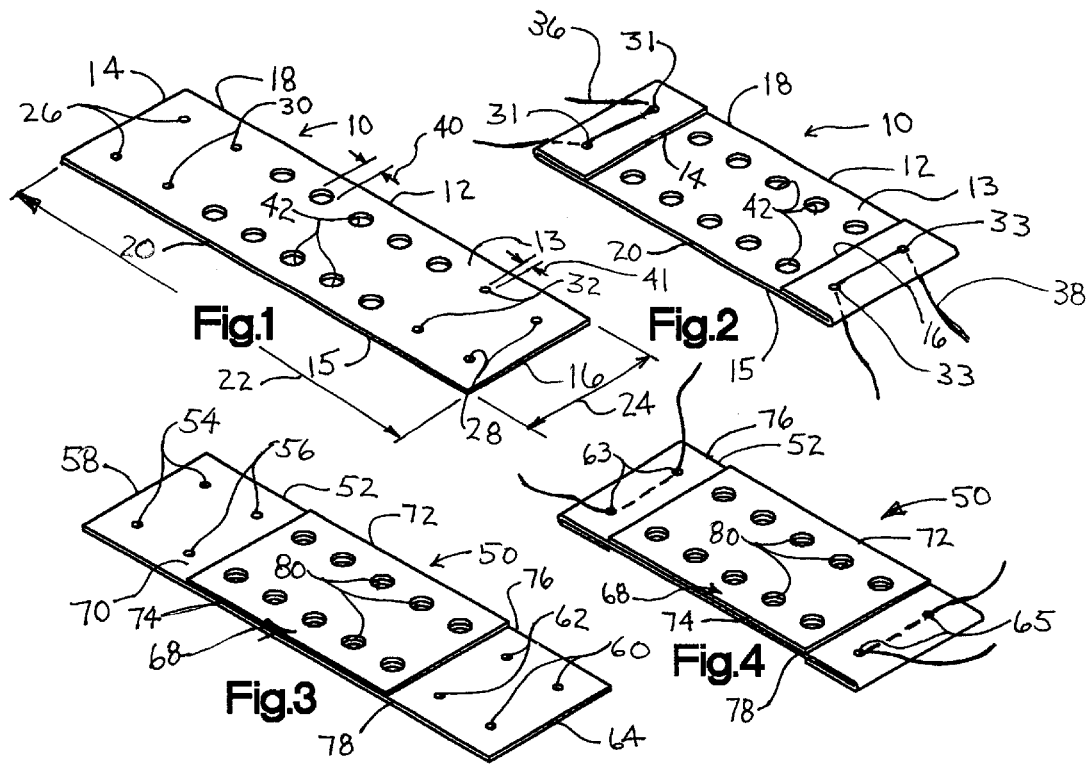
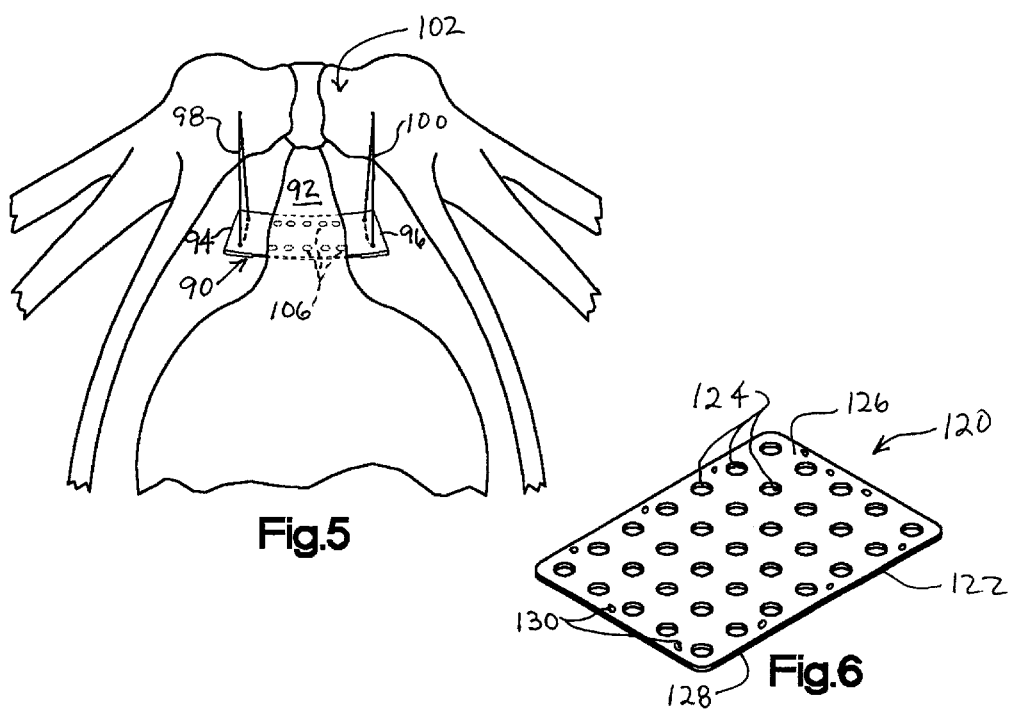

US 6,355,065 B1

IMPLANTABLE SUPPORT APPARATUS AND METHOD OF USING SAME

TECHNICAL FIELD

The present invention relates to an implantable support apparatus and to a method of using and to a method of making an implantable support apparatus.

BACKGROUND OF THE INVENTION

An implantable support, such as a sheet or patch of flexible material, is used to provide additional support to weakened or destabilized tissue of a patient. Such implantable supports are used to treat a variety of conditions, including, for example, closing hernias and providing suburethral stabilization. The support may be formed of biological tissue or a synthetic material.

Some materials currently being used to manufacture such supports fail to attach adequately to surrounding tissue or experience undesirable deformation after implantation. Such conditions often require an additional surgical procedure and/or result in discomfort to the patient.

In one particular procedure, commonly known as a transvaginal or pubovaginal sling procedure, a patch or strip of biological tissue is used to provide suburethral stabilization for female patients experiencing bladder dysfunction, such as stress urinary incontinence. However, ends of the strip are friable and tend to weaken or rupture upon penetration by a relatively large needle. In addition, conventional biological strips are not easily integrated into the surrounding tissue due to their biocompatibility.

SUMMARY OF THE INVENTION

One aspect of the present invention provides an implantable support apparatus that includes a sheet of flexible material having first and second end portions that are spaced apart from each other by a length of the material. First apertures extend through the sheet of material near each of the end portions. A plurality of second apertures, which preferably are larger than the first apertures, extend through an intermediate portion of the sheet of material located between the first and second end portions.

Another aspect of the present invention provides an implantable tissue support that includes a sheet of flexible, biocompatible biological tissue material. The sheet of tissue material has first and second end portions. The end portions are spaced apart from each other and a plurality of apertures are formed through the sheet at locations spaced from and intermediate the end portions of said sheet of tissue material.

Yet another aspect of the present invention provides a method of using an implantable sheet of biocompatible material. The method includes providing a sheet of flexible biocompatible material. First apertures are formed through the sheet near each of first and second end portions and a plurality of second apertures are formed through a portion of the sheet located intermediate the first and second end portions. Sutures are inserted through selected ones of the first apertures at the end portions for connection to desired tissue of the patient. The sheet of material is connected to the desired tissue using the sutures, whereby the patient's tissue engaging the intermediate portion of the sheet of material can embed itself into the second apertures to help hold the implanted sheet at a desired position.

Still another aspect of the present invention provides a method of making an implantable support apparatus. A sheet of flexible biocompatible material is provided. The sheet has first and second end portions that are spaced apart from each other by a length of the material. First apertures are formed through the sheet near each of the first and second end portions. A plurality of second apertures are formed through a portion of the sheet located intermediate the first and second end portions.

BRIEF DESCRIPTION OF THE DRAWINGS

The foregoing and other features of the present invention will become apparent to those skilled in the art to which the present invention relates upon reading the following description with reference to the accompanying drawings, wherein:

FIG. 1 is an isometric view of a support apparatus in accordance with a first embodiment of the present invention;

FIG. 2 is another view of the apparatus of FIG. 1 illustrating the end portions thereof in a folded condition;

FIG. 3 is an isometric view of a support apparatus in accordance with a second embodiment of the present invention;

FIG. 4 is another view of the apparatus of FIG. 3, illustrating the end portions thereof in a folded condition;

FIG. 5 is a top view of the apparatus of FIG. 4 illustrating an example of its in accordance with the present invention; and FIG. 6 is an isometric view of a support apparatus in accordance with a third embodiment of the present invention.

DESCRIPTION OF PREFERRED EMBODIMENTS

FIGS. 1 and 2 illustrate a first embodiment of an implantable support apparatus 10 in accordance with the present invention. The apparatus 10 is in the form of a substantially flat strip or sheet 12 of a flexible, biocompatible material. The sheet 12 has opposed surfaces 13 and 15 which, for purposes of simplicity of explanation, are shown to be substantially planar in the views of FIGS. 1 and 2.

The sheet 12 may be made of a synthetic material or a biological material, such as human fascia lata (e.g., homografts) or treated pericardium from animals (e.g., heterografts). Preferably, the biological material is glutaraldehyde cross-linked pericardium which has been substantially detoxified and rinsed with heparin. By way of example, the treated biological tissue may be a cytocompatible sheet of pericardium, such as the NO-REACT® Pericardial Patch or other tissue products commercially available from Shelhigh, Inc., of Millburn, New Jersey. Such pericardium may be bovine pericardium, porcine pericardium, or equine pericardium, although other types of treated biological tissue also may be used.

The sheet 12 includes end portions 14 and 16 that are spaced apart by elongated side edges 18 and 20. The side edges 18 and 20 extend a length of the sheet 12, indicated at 22. Similarly, the end portions 14 and 16 extend between the side edges 18 and 20 to define the width of the sheet 12, indicated at 24. The particular dimensions of the sheet 12 of material, including the width 24, length 22 and thickness thereof, may vary depending upon the intended use of the apparatus 10.

For example, the apparatus 10 may be used for closure of a hernia (see FIG. 6) in which the length may approximate its width. The apparatus 10 also may be used to provide desired support in a suburethral stabilization procedure (see FIG. 5) in which its length will be greater than its width. Accordingly, the apparatus may be fabricated in a variety of sizes, such as, for example, 2×7 cm, 2×10 cm, 5×5 cm, 6×8 cm, 6×10 cm, 10×15 cm, and 10×20 cm.

As shown in FIG. 1, a plurality of apertures 26 and 28 extend from one surface 13 of the sheet 12 to other surface 15 near each of the respective end portions 14 and 16. Preferably, two pairs of apertures 26 and 30 are formed through the sheet 12 near one end portion 14 and two pairs of apertures 28 and 32 are formed through the sheet near the other end portion 16. It is also contemplated that other numbers of apertures may be formed through the respective end portions 14 and 16.

Each aperture of each respective apertures pair 26, 28, 30, 32 is preferably spaced the same distance from its associated end portion 14, 16. In this embodiment, the apertures 26 and 28 are located closer to their respective end portions 14 and 16 than are the other associated pairs of respective apertures 30 and 32. In particular, each of the apertures 26, 28 is configured to align substantially coaxially with an associated one of the respective apertures 30, 32 when the end portions are folded, as shown in FIG. 2. That is, each of the end portions 14, 16 may be folded on itself transverse to a long axis of the sheet 12 and toward the opposed end portion 16, 14 to provide overlapping layers at the corresponding ends of the apparatus 10.

As shown in FIG. 2, the aligned apertures provide suture holes 31 and 33 that extend coaxially through the overlapping layers of the sheet 12 near the end portions 14 and 16. The overlapping layers of the sheet 12 at the folded ends increases the thickness of the apparatus 10 at the respective end portions. This reinforces the suture holes 31 and 33 and, in turn, helps prevent tearing and fraying when the apparatus 10 is implanted. Consequently, the longevity of the apparatus 10 also is improved.

The apertures 26, 28, 30, and 32 are dimensioned and configured for receiving a needle and/or a suture filament through the apertures. Accordingly, cross-sectional diameter of the apertures 26, 28, 30, and 32 may vary based on the desired size of sutures to be used during implantation of the apparatus 10. As shown in FIG. 2, sutures 36 and 38 are threaded through the respective suture holes 31 and 33 to secure the apparatus 10 to desired tissue of the patient, such as to bone, muscle, or connective tissue.

The apparatus 10 also includes a plurality of other apertures 42, which are larger than the apertures 26, 28, 30, and 32. The apertures 42 are formed through an intermediate portion of the sheet 12 spaced from and located between each of the end portions 14 and 16.

The apertures 42 have cylindrical sidewall portions that extend axially between the surfaces 13 and 15. The axial length of the sidewall portions of each aperture 42, thus, is defined by the thickness of the sheet 12. As shown in FIG. 1, the cylindrical sidewall of each aperture 12 has a diameter 40 that is greater than the diameter 41 of the apertures 26, 28, 30, and 32 located at the end portions 14 and 16. For example, each of the apertures 42 has a diameter 40 ranging from about 2 mm to about 5 mm, and the diameter 41 of apertures 26, 28, 30, and 32 range from about 0.5 mm to about 2 mm.

While each of the apertures 26, 28, 30, 32, 42 is illustrated as a right, circular cylinder, each such aperture also could have another cross-sectional shape, such as a rectangular or polygonal cylinder or conical. In addition, while the apertures 42 are illustrated as being of uniform diameter, apertures having various diameters may be used on a single apparatus 10 with equal facility. The apertures 42 also could be randomly spaced along the intermediate portion of the strip 12 instead of the discrete rows of apertures shown in the figures.

FIGS. 3 and 4 illustrate another embodiment of an apparatus 50 in accordance with the present invention. The apparatus 50 includes an elongated sheet 52 of a flexible, biocompatible material that is substantially identical to the sheet 12 shown and described with respect to FIGS. 1 and 2.

Referring to FIG. 3, briefly stated, the sheet 52 has first and second pairs of apertures 54 and 56 formed through the sheet near one end portion 58 and third and fourth pairs of apertures 60 and 62 formed through the sheet near the other end portion 64. Corresponding ones of the apertures align with each other when the end portions are folded, shown in FIG. 4, to provide reinforced suture holes 63 and 65 near opposed ends of the apparatus 50.

In this embodiment, the apparatus 50 also includes an additional sheet 68 of a biocompatible tissue material. The sheet 68 preferably is formed of a cytocompatible material identical to the material forming the other sheet 52, e.g., glutaraldehyde cross-linked pericardium which has been detoxified.

As shown in FIG. 3, the additional sheet 68 is attached to a surface 70 of the sheet 52. The sheet 68 extends longitudinally along an intermediate portion of the sheet 52 located between the apertures 56 and 62. The sheet 68 also has side edges 72 and 74 positioned at respective side edges 76 and 78 of the other sheet 52. The sheets 52 and 68 are connected together, such as by sutures (not shown) or a suitable surgical adhesive. The sheet 68 helps to reduce deformation and folding of the apparatus 50 along its long axis when implanted.

A plurality of apertures 80 also are formed through both of the sheets 52 and 58, such as shown in FIGS. 3 and 4. The apertures 80 are substantially identical to the apertures (e.g., 42) shown and described with respect to in FIGS. 1 and 2, although they have longer sidewall portions due to the increased thickness of the apparatus provided by the two sheets 52 and 68.

It will be appreciated that the sheet 68 also could be dimensioned and configured to extend coextensively with the sheet 52. In this configuration, all the apertures extend completely through both sheets. The coextensive layers of such sheets 52 and 68, thus, eliminate the need to fold the end portions as shown in FIG. 4.

FIG. 5 illustrates an example of an intended use of an implantable support apparatus 90, in accordance with the present invention. Here, the apparatus 90 is used as a suburethral stabilization sling for helping to reduce stress incontinence in women. In particular, the support apparatus 90 is inserted into a passage or tunnel extending through the vaginal mucosa adjacent the urethra 92. The support apparatus 90 is passed through the tunnel so that the intermediate portion located between end portions 94 and 96 thereof is positioned transverse to and supports the urethra 92. The end portions 94 and 96 are folded, as shown in FIGS. 2 and 4, to inhibit fraying or rupturing after being implanted.

Sutures 98 and 100 are inserted through the suture holes formed in the folded end portions 94 and 96 of the apparatus 90, as described above. The sutures 98 and 100 are used to place the apparatus 90 at a desired position relative to the urethra 92. In particular, the sutures 98 and 100 stabilize the end portions 94 and 96 of the support apparatus 90 by being affixed to desired tissue of the patient, such as to the pubic bone 102 or to surrounding abdominal muscles.

An example of a vaginal sling procedure is disclosed in the in 1997 instructional materials entitled: In-Fast Bone Screw System for transvaginal cystourethropexy and vaginal sling procedure, Instructions for use, which is available from Influence, Inc., of San Francisco, Calif., the content of which instructional material is incorporated herein by reference.

The suture holes formed through the folded end portions 94 and 96 facilitate threading the sutures 98 and 100 through the end portions, shown in FIG. 5. The sutures 98 and 100 may be threaded through the suture holes without the use of a needle. Using a needle to penetrate such tissue might result in undesirable fracturing or rupturing of the tissue at the end portions.

The sutures 98 and 100 are tied off so that the support apparatus 90 urges or elevates the urethra toward the posterior surface of a pubic bone to help reduce the effects of urinary stress incontinence. The particular amount tension needed to properly support the urethra is explored in greater detail in Use of the Fascial Sling for Neurogenic Incontinence: Lessons Learned, The Journal of Urology, Vol. 150, 683-386 (1993).

The larger apertures 106 formed through the intermediate portion of the apparatus 90 permit developing scar tissue to embed within and/or pass through the biocompatible tissue strip. This helps to straighten the elongated central portion of the apparatus 90 and promote integration of the apparatus into the surrounding tissue.

Because the tissue is biocompatible, in the absence of such apertures 106, scar tissue would tend to form between the support apparatus 90 and the patient's tissue that is in contact with the apparatus. The formation of scar tissue might cause an implanted biocompatible apparatus (without the apertures 106) to be urged away from the tissue being supported thereby. For the suburethral stabilization procedure, the formation of scar tissue could result in further tightening of the sling apparatus 90, which would cause additional discomfort and/or incontinence to the patient.

FIG. 6 illustrates another embodiment of a support apparatus 120, in accordance with the present invention, which may be used in various surgical applications. The support apparatus 120, for example, may be used to close hernias or support other organs or tissue.

The apparatus 120 is formed of flexible, biocompatible material that is substantially identical to the material shown and described with respect to FIGS. 1–4. The apparatus 120 preferably is formed of a sheet 122 of biological material having a plurality of apertures 124 extending between the opposed surfaces 126 and 128 of the sheet. The apertures 124 typically have diameters ranging from about 2 mm to about 5 mm. The apertures 124 permit scar tissue to grow into and embed therein which improves integration of the apparatus 120 into the patient's body. This provides desired adhesion between the biocompatible tissue material of the apparatus 120 and the patient's surrounding tissue to help hold the sheet 122 at a desired position.

A plurality of suture holes 130 also may be formed through the sheet 122 along the perimeter portion of the sheet. The suture holes 130 facilitate threading sutures through the sheet 122. The suture holes 130 also inhibit fraying that might occur along its perimeter portion when penetrated by a relatively large needle during implantation of the tissue sheet 122.

In view of the foregoing, each of the embodiments shown in FIGS. 1–6 provide an implantable support apparatus with the advantages of cytocompatibility which, when implanted, also permits integration and adhesion of the apparatus into surrounding tissue. In particular, apertures are formed through the sheet of tissue material to permit scar tissue to grow into and embed itself within such apertures. This results in improved healing and a lower likelihood of re-operation.

Further, because the apertures at the ends of the apparatus provide suture holes, regardless of whether the end portions are folded (FIGS. 2 and 4) or are unfolded (FIGS. 1 and 3), sutures conveniently may be fed through selected apertures without the use of a needle. A needle, if needed during implantation, may be threaded onto sutures before or after the suture is fed through the suture holes. The suture holes also inhibit rupturing and fraying along the end portions of the apparatus.

The various apertures may be formed through a respective sheet of the apparatus by cutting or punching holes in a known manner. The apertures may be formed before, during or after treating the tissue so as to render it biocompatible.

From the above description of the invention, those skilled in the art will perceive improvements, changes and modifications. Such improvements, changes and modifications within the skill of the art are intended to be covered by the appended claims.

Having described the invention, the following is claimed:

1. An implantable support apparatus comprising:
a sheet of a flexible biocompatible material having first and second end portions, said first and second end portions of said sheet being spaced apart by a length of said material, a first plurality of first apertures extending through said sheet near said first end portion and a second plurality of said first apertures formed through said sheet near said second end portion, a plurality of second apertures formed through an intermediate portion of said sheet spaced from and located intermediate said first and second pairs of first apertures wherein said plurality of second apertures being different from said plurality of first apertures.

2. An apparatus as set forth in claim 1 wherein said biocompatible material is a biological tissue material.

3. An apparatus as set forth in claim 2 wherein said biological tissue material is pericardium.

4. An apparatus as set forth in claim 2 further including a third pair of said first apertures extending through a part of said sheet located between said plurality of second apertures and said first pair of said first apertures, a fourth pair of said first apertures extending through a part of said sheet located between said plurality of second apertures and said second pair of said first apertures, each of said first and second pairs of first apertures being arranged for alignment with the respective third and fourth pairs of said first apertures so that, upon folding a part of each of said first and second end portions toward the opposite end portion, a folded end portion is formed at each end of said sheet with aligned ones of said first apertures providing reinforced suture holes that extend through each of said folded end portions.

5. An apparatus as set forth in claim 2 wherein each of said second apertures has a cylindrical sidewall extending between first and second surfaces of said sheet, said cylindrical sidewall of said second apertures having a diameter that is greater than the diameter of each of said first apertures so that, when implanted, surrounding tissue embeds into said second apertures to facilitate integration of said apparatus into the surrounding tissue.

6. An apparatus as set forth in claim 5 wherein said sheet of biological material is a first sheet and said apparatus further includes a second sheet of biocompatible material connected over a surface of said first sheet intermediate said first and second end portions of said first sheet, said second apertures extending through both said first sheet and said second sheet.

7. An implantable tissue support apparatus comprising:
- a sheet of flexible, biocompatible biological tissue material having first and second end portions, said first and second end portions of said sheet being spaced apart by a length of said tissue material; and
- a plurality of apertures formed through said sheet at locations spaced from and intermediate said end portions of said sheet.

8. An apparatus as set forth in claim 7 wherein said sheet of tissue material is a first sheet and said support further includes a second sheet of biocompatible tissue material connected over at least part of a surface of said first sheet intermediate said first and second end portions of said first sheet, said plurality of apertures being formed through both said first sheet and said second sheet.

9. An apparatus as set forth in claim 8 further including suture holes formed through said first sheet of tissue material near each of said end portions, each of said suture holes having a diameter that is less than the diameter of each of said plurality of apertures.

10. An implantable support apparatus comprising:
- a sheet of a flexible biocompatible material having first and second end portions, said first and second end portions of said sheet being spaced apart by a length of said material, a first pair of first apertures extending through said sheet near said first end portion and a second set of said first apertures extending through said sheet near said second end portion, a plurality of second apertures extending through an intermediate portion of said sheet spaced from and located intermediate said first and second sets of first apertures, a third set of said first apertures extending through a part of said sheet located between said plurality of second apertures and said first set of said first apertures, a fourth set of said first apertures extending through a part of said sheet located between said plurality of second apertures and said second set of said first apertures, each of said first and second sets of first apertures being arranged for alignment with the respective third and fourth sets of said first apertures so that, upon folding a part of each of said first and second end portions toward the opposite end portion, a folded end portion is formed at each end of said sheet with aligned ones of said first apertures providing reinforced suture holes that extend through each of said folded end portions.

11. An implantable support apparatus comprising:
- a sheet of a flexible biocompatible material having first and second end portions, said first and second end portions of said sheet being spaced apart by a length of said material, a first set of first apertures extending through said sheet near said first end portion and a second set of said first apertures extending through said sheet near said second end portion, a plurality of second apertures extending through an intermediate portion of said sheet spaced from and located intermediate said first and second sets of first apertures, each of said second apertures having a cylindrical sidewall extending between first and second surfaces of said sheet, said cylindrical sidewall of said second apertures having a diameter that is greater than the diameter of each of said first apertures so that, when implanted, surrounding tissue embeds into said second apertures to facilitate integration of said apparatus into the surrounding tissue.

12. An implantable support apparatus comprising:
- a first sheet of a flexible biocompatible material having first and second end portions, said first and second end portions of said sheet being spaced apart by a length of said material, a first set of first apertures extending through said sheet near said first end portion and a second set of said first apertures extending through said sheet near said second end portion, a plurality of second apertures extending through an intermediate portion of said sheet spaced from and located intermediate said first and second sets of first apertures; and
- a second sheet of biocompatible material connected over a surface of said first sheet intermediate said first and second end portions of said first sheet, said second apertures extending through both said first sheet and said second sheet.

* * * * *